United States Patent
Portney

(10) Patent No.: US 6,500,181 B1
(45) Date of Patent: Dec. 31, 2002

(54) INSTRUMENT FOR FOLDING AND INSERTING ANTERIOR CHAMBER INTRAOCULAR LENSES

(76) Inventor: Valdemar Portney, 11940 N. Riviera, Tustin, CA (US) 92782

( * ) Notice: Subject to any disclaimer, the term of this patent is extended or adjusted under 35 U.S.C. 154(b) by 241 days.

(21) Appl. No.: 09/690,783

(22) Filed: Oct. 17, 2000

(51) Int. Cl.⁷ ................................................ A61F 9/00
(52) U.S. Cl. .................................... 606/107; 623/6.12
(58) Field of Search .................... 606/107, 6; 623/6.12, 623/6.18, 6.19, 6.2, 6.21; 604/57, 59, 294

(56) References Cited

U.S. PATENT DOCUMENTS

| | | | | |
|---|---|---|---|---|
| 4,747,404 A | * | 5/1988 | Jampel et al. ............... | 250/221 |
| 4,819,631 A | * | 4/1989 | Poley ........................... | 606/107 |
| 5,354,333 A | * | 10/1994 | Kammann et al. .......... | 606/107 |
| 5,653,753 A | * | 8/1997 | Brady et al. ................. | 606/107 |
| 5,702,400 A | * | 12/1997 | Brown et al. ................ | 606/107 |
| 5,702,402 A | * | 12/1997 | Brady ........................... | 606/107 |
| 5,711,317 A | * | 1/1998 | McDonald .................... | 606/107 |
| 6,283,976 B1 | * | 9/2001 | Portney ........................ | 606/107 |
| 6,334,862 B1 | * | 1/2002 | Vidal et al. ................... | 606/107 |
| 6,336,932 B1 | * | 1/2002 | Figueroa et al. ............. | 606/107 |
| 6,355,046 B2 | * | 3/2002 | Kikuchi et al. .............. | 606/107 |
| 6,371,960 B2 | * | 4/2002 | Heyman et al. ............. | 606/107 |
| 6,428,545 B2 | * | 8/2002 | Portney ........................ | 606/107 |

* cited by examiner

*Primary Examiner*—Danny Worrell
(74) *Attorney, Agent, or Firm*—Howard R. Lambert

(57) ABSTRACT

There is described an instrument for double folding an elastically deformable intraocular lens (IOL) into a general C-shape for insertion through a small incision into the anterior chamber of a patient's eye for controlled unfolding. The instrument comprises an elongate, slender IOL insertion tube having an IOL receiving station located in the tube adjacent a cutaway opening. A support element is provided for holding a central optic region of an IOL received in the IOL receiving station against an inner surface of the tube during the double folding of the IOL. An IOL double folding member installed on the tube has a converging recess facing the IOL receiving station, the recess being along the longitudinal tube axis and having an IOL discharge opening facing the insertion tube distal end. In one version, the IOL double folding member is moved along the insertion tube to cause double folding of the IOL held in the IOL receiving station; in another version, the IOL is moved through the insertion tube into the double folding member that is fixed to the tube. A disposal IOL insertion tip is attached at the distal end of the insertion tube and is sized for passing through an ocular incision no greater than about 3.2 mm.

25 Claims, 10 Drawing Sheets

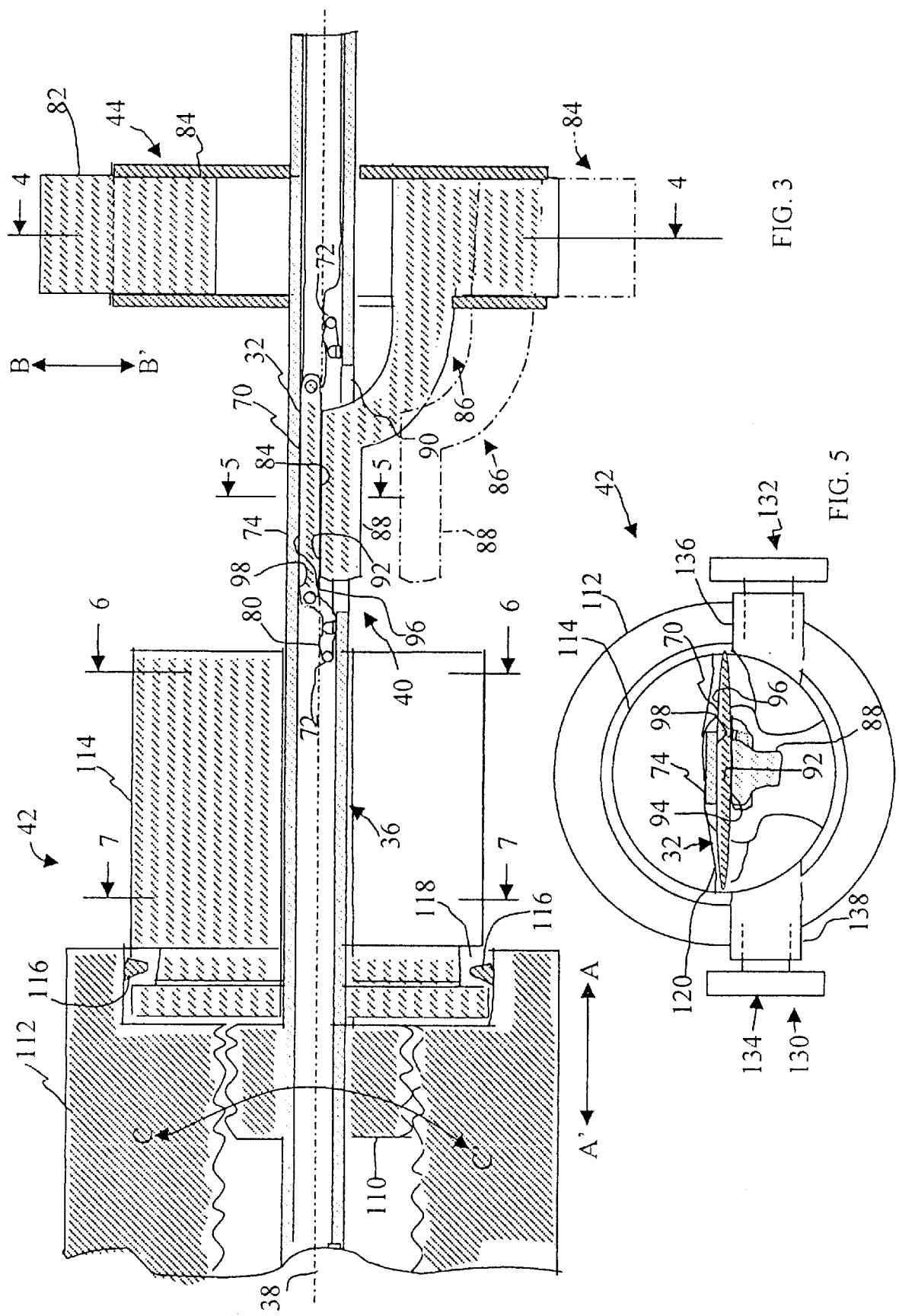

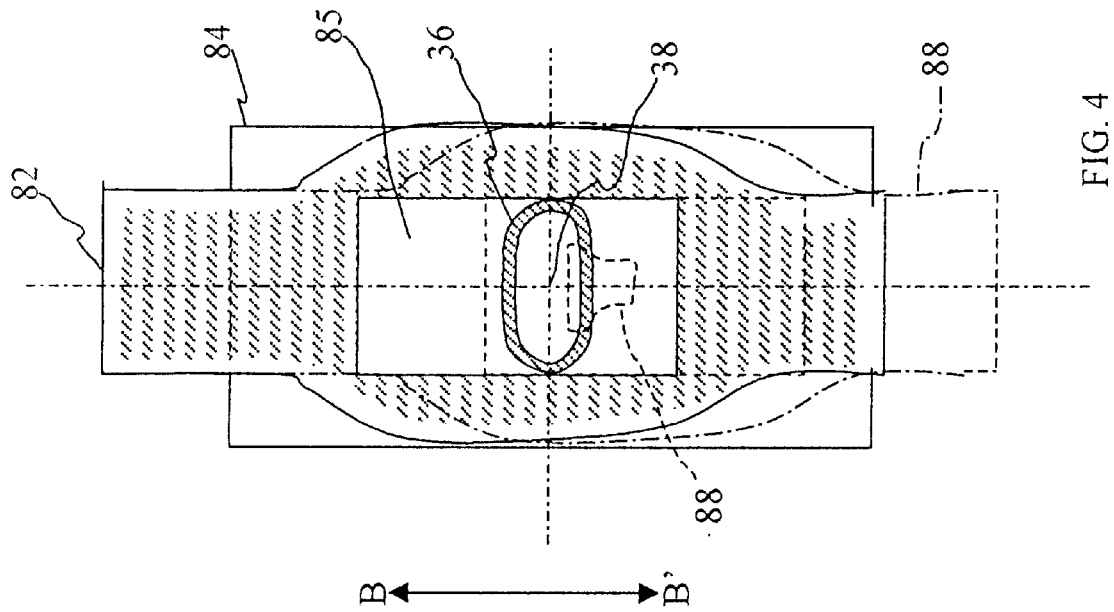
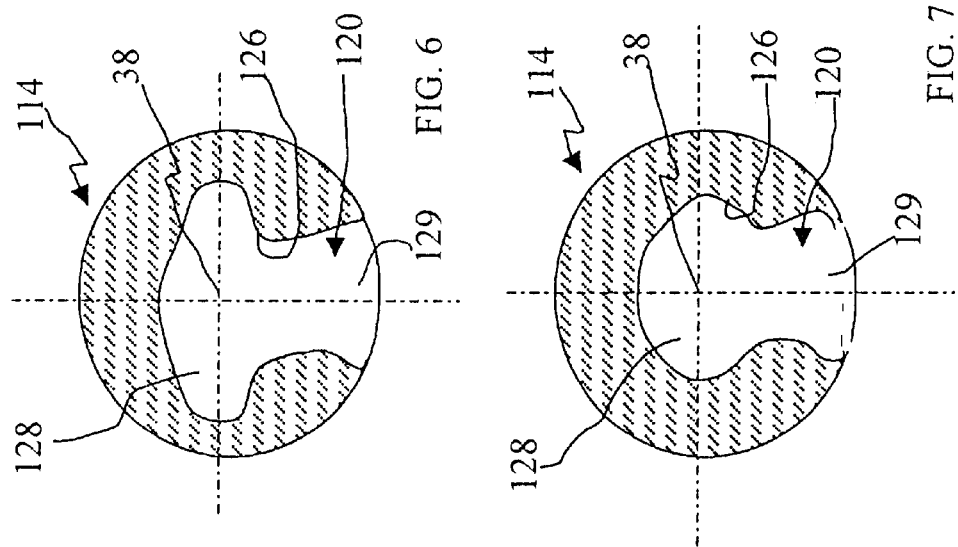

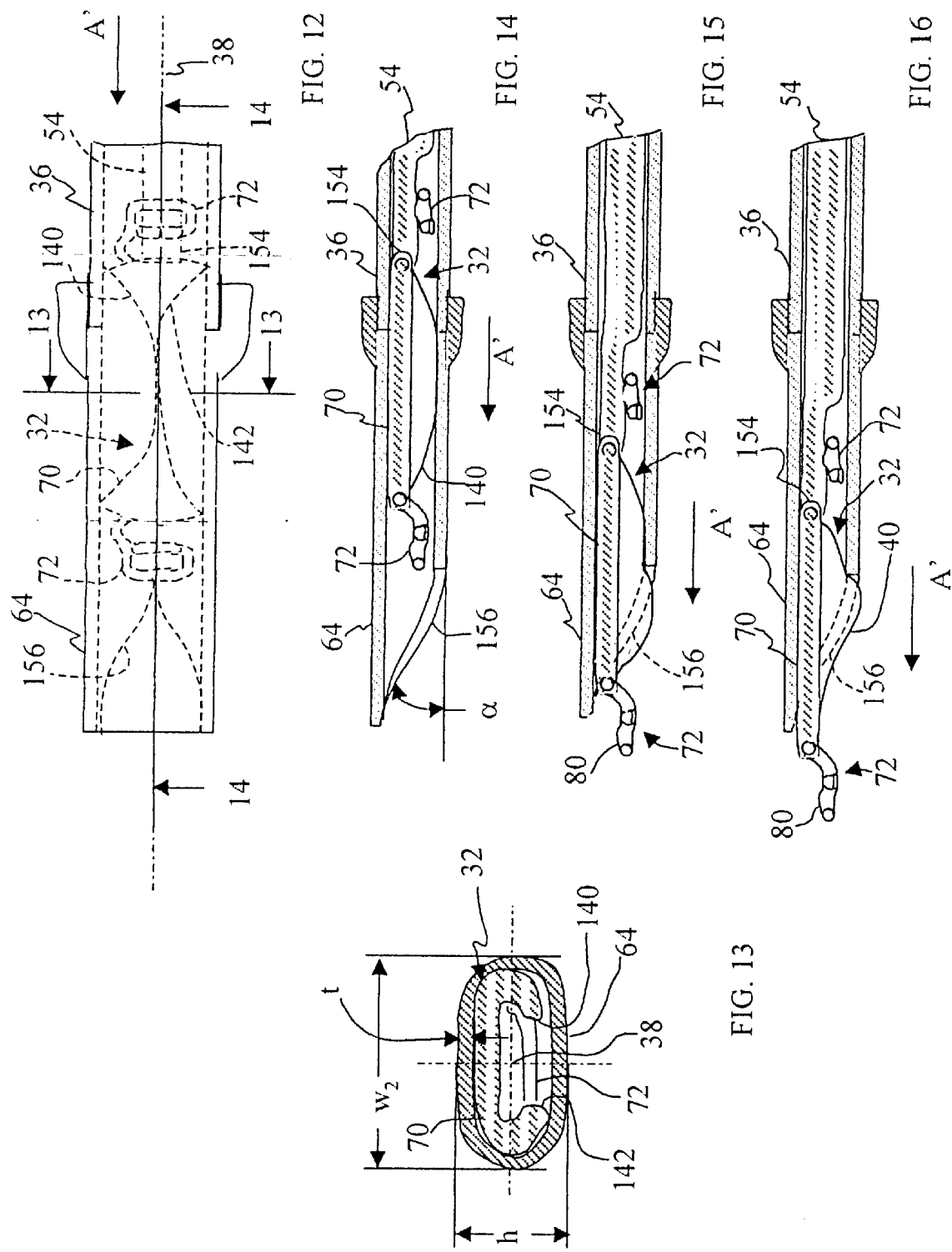

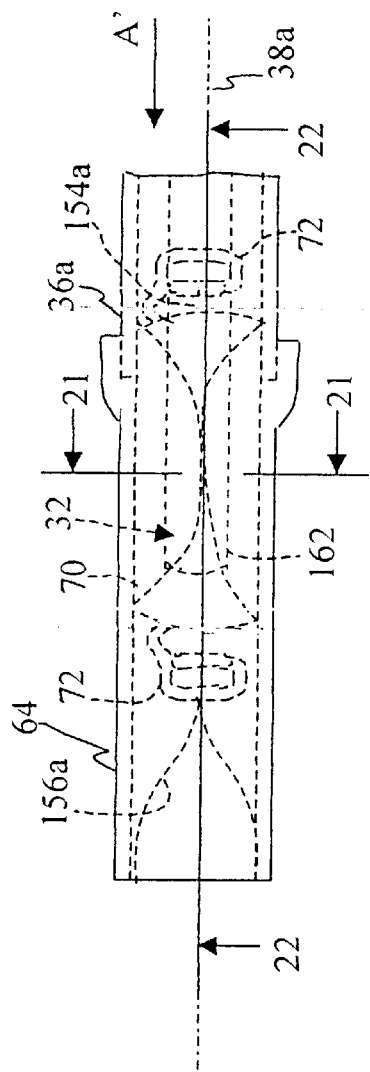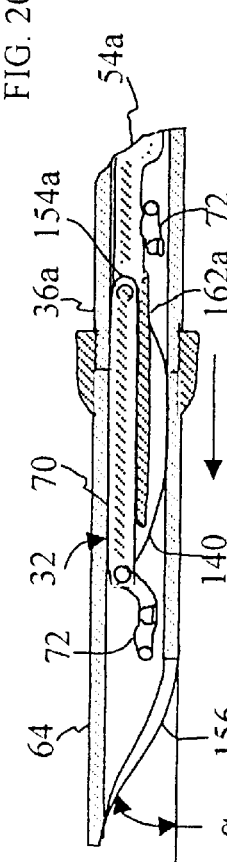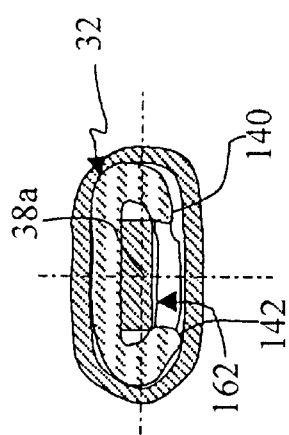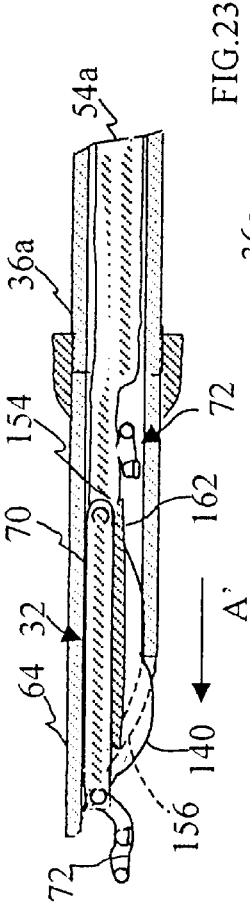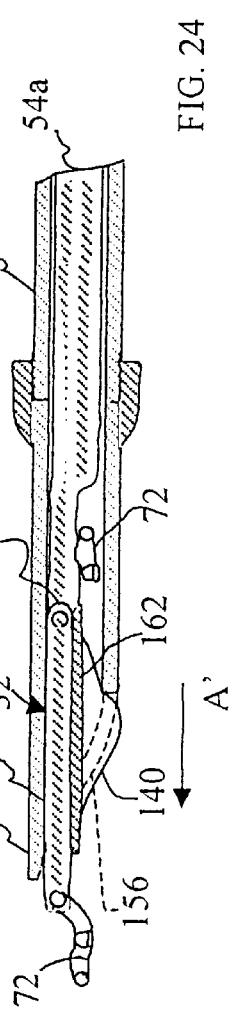

INSTRUMENT FOR FOLDING AND INSERTING ANTERIOR CHAMBER INTRAOCULAR LENSES

BACKGROUND OF THE INVENTION

1. Field of the Invention

The present invention relates generally to the field of ophthalmic, more particularly to intraocular lenses (IOLs), and still more particularly to instruments for implanting IOLs in patient's eyes.

2. Background Discussion

Consideration of the term "phakic," which refers an eye in which the natural ocular lens is still present, may be helpful to the understanding of the present invention. The term "phakic" is in contrast to the term "aphakic" which refers to an eye from which the natural ocular lens has been removed.

A phakic eye is considered a dynamic or active eye because the existing natural lens is a living part of an eye, and is therefore subject to change over time due to such biological effects as disease or aging. An aphakic eye, on the other hand, is considered a static eye because the natural lens has been removed and thus is no longer subject to biological effects that would otherwise affect the natural lens.

Vision in a phakic eye is caused by light from a viewed object being refracted by the cornea and the natural lens located rearward of the cornea to form an image on the retina at the back of the eye. Such image formation may, for example, be assisted by corrective spectacles, contact lens or corneal reshaping.

A common ocular problem in a phakic eye is impaired vision due to the natural lens becoming cloudy or opaque—a degenerative condition known as "cataract." Cataracts typically form with aging, with most individuals over about 60 years old suffering from cataracts to at least some extent. Cataracts can, however, also occur as a result of trauma, systemic diseases (such as diabetes), ocular diseases, long term steroid therapy, excessive exposure to ultra violet light, and heredity.

So far as is presently known, cataracts cannot be cured, reduced, or even significantly arrested. Corrective treatment for cataracts therefore requires the surgical extraction of the natural lens when the lens becomes so cloudy that vision in the afflicted eye becomes so impaired as to affect the patient's life style. In this manner a phakic eye becomes an aphakic eye.

After a diseased or defective natural lens has been surgically removed, the typical current vision-restoring treatment is to implant in the aphakic eye a prosthetic lens, called an intraocular lens (IOL), that substitute for the removed natural lens and mimics some of its optical characteristics.

Typical IOLs are constructed having an transparent optic with attached fixation members for maintaining the optical axis of the optic aligned with the optical axis of the eye.

Prior to IOL development (in about the mid-1940's) thick, high diopter spectacles had to be worn to restore vision in aphakic eyes. However, most patients dislike such spectacles (which may still be needed in some special circumstances in which the implanting of IOLs is not feasible) because of their weight and unattractive appearance.

For a long time, IOLs were typically constructed from a rigid, biocompatible polymethyl methacrylate (PMMA) plastic material. Rigid PMMA IOLs require implanting through relatively large surgical incision in the eye, usually, the same incision required for removing the natural lens in one piece from the eye.

However, with the development in the 1970's of a phacoemulsification process for ultrasonically breaking up natural lenses to enable their removal through much smaller ocular incisions than had previously been required to remove intact natural lenses. This phacoemulsification process gave immediate rise to the development of small incision, elastically deformable IOLs made of silicone or acrylic. It will be appreciated that small, sutureless ocular incisions, currently as small as about 3.2 to 3.5 mm, surgically made for natural lens extraction and IOL implanting are highly desirable for minimizing trauma to the eye, reducing the possibility of such complications as infection, and speeding patient recovery.

Recently and importantly, in addition to the implanting of IOLs in aphakic eyes to restore vision after removal of the natural lens, there has been considerable interest in developing techniques for implanting IOLs in phakic eyes to correct myopia, hypermetropia, presbyopia and astigmatism associated with non-cataract phakic eyes. Such implanting of corrective IOLs in phakic eyes can obviate the wearing of spectacles or contact lenses, which are troublesome and, in fact, may limit certain activities and professions, or having permanent surgical cornea reshaping, which may not be desired by or feasible for many individuals.

In an aphakic eyes, unless unusual conditions are encountered, IOLs are implanted in the posterior chamber of the eye (i.e., the "bag") from which the natural lens has been removed in order to mimic the natural lens as much as possible. In contrast, corrective IOLs for phakic eyes are desirably implanted in the anterior chamber of the eyes (between the cornea and the iris) because the posterior chamber is still occupied by the natural lens.

Elastically deformable anterior chamber IOLs, to which this present invention indirectly relates, are similar in many respects to current elastically deformable posterior chamber IOLs. However, anterior chamber IOLs are usually much more difficult to implant.

A significant anterior chamber IOL implanting problem relates to the unfolding of elastically deformed IOLs from known IOL inserters into the anterior chamber of the eye, in which the typical axial separation between the cornea and natural crystalline lens is only about 2 mm.

Typical known IOL inserters single fold elastically deformable IOLs in half across the optic, creating what is commonly referred to as a "taco" fold. A "taco" folded IOL requires a space (along the optical axis) equal to one-half the diameter of the optic for the IOL to unfold into. For example, a "taco" folded IOL having a typical optic diameter of 6 mm requires a 3 mm axial space for unfolding. It is thus inevitable that the unfolding of a single folded elastically deformable IOL in the anterior chamber will cause unintentional contact with, and likely injury to, the sensitive posterior endothelial surface of the cornea and/or the anterior surface of the crystalline lens.

A principal objective of the present invention is, thus to provide an IOL insertion instrument that double folds an elastically deformable anterior chamber IOL so that the IOL requires substantially less axial unfolding space in the anterior chamber than does a single folded IOL. Because the double folded IOL having a 6 mm diameter optic requires only about 1.5 mm of anterior chamber axial unfolding space, the possibility of the unfolding optic unintentionally contacting and injuring the endothelial cell surface of the cornea and/or the anterior surface of the crystalline lens is minimized.

SUMMARY OF THE INVENTION

In accordance with the present invention, there is provided an instrument for double folding an elastically deformable intraocular lens (IOL) and for inserting said double folded IOL into the anterior chamber of a patient's eye for controlled unfolding. The instrument comprises an elongate, slender IOL insertion tube having a distal end and a longitudinal axis, an IOL receiving station located in the tube adjacent a cutaway opening in the tube, and a support element configured for holding a central optic region of an IOL received in the IOL receiving station against an inner surface of the tube during double folding of the IOL. Included is an IOL double folding member installed on the tube, the folding member having a converging recess facing the IOL receiving station, the recess being along the tube longitudinal axis and having an IOL discharge opening facing the IOL insertion tube distal end.

Means are included for causing relative axial movement between an IOL received in the IOL receiving station and the IOL double folding member to cause the double folding of the IOL into a general C-shape. A piston is axially slidably disposed in the tube for axially pushing the double folded IOL through the distal end of the tube.

A disposal IOL insertion tip, sized for insertion through an ocular incision no greater than about 3.2 mm, is preferably detachably attached to a distal end of the IOL insertion tube, the insertion tip being flexible and constructed of a silicone or an acrylic material. The insertion tip has an oval cross section having an external width between about two times and three times greater than an external height of the tip. The distal end of the IOL insertion tip is beveled at an angle between about 30 degrees and about 45 degrees to permit gradual and controlled unfolding of the IOL after insertion into an eye.

In accordance with a preferred embodiment of the invention, the IOL folding member is axially movable on said tube and the means for causing relative axial movement between the IOL and the IOL folding member is connected for causing the IOL folding member to move axially along the IOL insertion tube so that the converging recess moves onto the IOL received in the IOL receiving station member, thereby causing the double folding of the IOL received in received IOL receiving station. Further, the means for causing relative movement includes a drive member threadably connected to the tube and in driving engagement with the IOL folding member for causing axial movement thereof.

The support element includes an IOL support member movable between a first position in which the support element permits the insertion of an IOL into the IOL receiving station through the tube cutaway opening and a second position in which the support element holds a central optic region of the IOL against the tube inner surface parallel to said tube longitudinal axis.

Means cooperating with the IOL folding member may be provided for exerting a side pressure on the IOL after being double folded in a general C-shape to thereby compress the double folded IOL into a tighter C-shape.

In a variation instrument, the IOL double folding member is fixed to the IOL insertion tube and the means for causing relative axial movement between an IOL received in the IOL receiving station and the double folding member causes the IOL received in the IOL receiving station to be moved axially through the IOL insertion tube into the converging recess of the IOL double folding member. The means for causing relative axial movement comprises a piston axially slidably disposed in the tube, a distal end of the piston being configured for engaging an edge of an optic portion of an IOL received in the receiving station. In this variation instrument, the support element comprises a slender, axial projection at the piston distal end.

More specifically, in accordance with a preferred embodiment, there is provided the instrument for double folding an elastically deformable intraocular lens (IOL) and for inserting the double folded IOL into the anterior chamber of a patient's eye for controlled unfolding, comprises an elongate, slender IOL insertion tube having a distal end and a longitudinal axis and an IOL receiving and folding station located inside the tube adjacent a side opening in the tube. The IOL receiving and folding station is configured for receiving an IOL which has an optic and haptics attached to opposing edges of the optic, with the haptics generally aligned with the IOL insertion tube longitudinal axis. Included is an IOL double folding member axially movably mounted on the IOL insertion tube, the IOL double folding member having a converging recess facing the IOL receiving and folding station and an IOL discharge opening facing the distal end of the tube, the recess being along the longitudinal axis of the tube. A driver is threadably installed on an externally threaded element fixed to the IOL insertion tube and is coupled to the IOL double folding member for causing movement of IOL double folding member axially along the IOL insertion tube between a first axial position in which the member is out of engagement with an IOL received in the IOL receiving and folding station and a second axial position in which the member causes the double folding of an IOL received in the station into a general C-shape.

The means for axially moving said IOL folding member between said folding member first and second positions includes an externally threaded member fixed to said IOL insertion tube, said driver being threadably installed on said externally threaded element.

Means are included for axially pushing a double folded IOL positioned in the IOL receiving and folding station through the IOL double folding member discharge opening and the distal end of the tube. An IOL support member having an IOL support element is movable between a first position in which the support element permits the insertion of an IOL into the IOL receiving and folding station through the tube cutaway opening and a second position in which the support element holds a central optic region of the IOL against an inner surface of the tube parallel to the tube longitudinal axis as the IOL is double folded. Preferably, means cooperating with the IOL folding member are included for exerting a side pressure on the IOL after being double folded into a general C-shape to thereby compress the double folded IOL into a tighter C-shape.

Further included are a disposable IOL insertion tip and means for detachably attaching the insertion tip to the IOL insertion tube distal end. The insertion tip has an oval transverse cross sectional shape with an external width that is about 2 to about 3 times greater than an external height, a wide region of the insertion tip being thereby formed; the insertion tip being sized for insertion through an ocular incision no greater than about 3.2 mm. The wide region of the IOL insertion tube distal end is preferably beveled at an angle between about 30 and about 45 degrees A variation instrument for double folding an elastically deformable intraocular lens (IOL) and for inserting said double folded IOL into the anterior chamber of a patient's eye for controlled unfolding comprises an elongate, slender IOL insertion tube having a distal end and a longitudinal axis, and IOL receiving station located inside the tube adjacent a side opening in the tube. The IOL receiving station is configured for receiving an IOL, which has an optic and haptics attached to opposing edges of the optic, with the haptics generally aligned with the IOL insertion tube longitudinal axis.

Additionally included is an IOL double folding member fixed to the IOL insertion tube and having a converging IOL engaging recess with a wide opening facing the IOL receiving station and a discharge opening facing the distal end of the IOL insertion tube, the recess being along the tube longitudinal axis. Provided is a support member configured for holding a central optic region of an IOL received in the IOL receiving station against an inner surface of said IOL insertion tube along a line parallel to the insertion tube longitudinal axis. A piston is installed in the IOL insertion tube for axially pushing the IOL received in the IOL receiving station along the tube and into the IOL double folding member converging recess for causing the double folding of the IOL into a general C-shape, and for thereafter pushing the double folded IOL through the distal end of the tube. The support member is formed as an axial projection at the distal end of the piston.

Preferably there are included a disposable IOL insertion tip and means for detachably attaching the insertion tip to the IOL insertion tube distal, the insertion tip having an oval transverse cross sectional shape with an external width that is about 2 to about 3 times greater than an external height, a wide region of the insertion tip being thereby formed, and being sized for insertion through an ocular incision no greater than about 3.2 mm. The wide region of the IOL insertion tube distal end is beveled at an angle between about 30 and about 45 degrees.

BRIEF DESCRIPTION OF THE DRAWINGS

The present invention can be more readily understood by a consideration of the following detailed description when taken in conjunction with the accompanying drawings, in which:

FIG. 3 is a longitudinal cross sectional drawing looking along line 3—3 of FIG. 2, showing the IOL received into the IOL receiving and folding region and showing IOL double folding means and IOL holding means and showing a n IOL holding member finger positioned for holding the received IOL against an inner wall surface of the IOL insertion tube;

FIG. 4 is a vertical cross sectional drawing looking along line 4—4 of FIG. 3, showing the IOL holding member in a vertical sliding relationship with the IOL insertion tube;

FIG. 5 is a vertical cross sectional drawing looking along line 5—5 of FIG. 3, showing the IOL held in the IOL holding and folding station and showing a transverse IOL compressing member associated with the IOL double folding member;

FIG. 6 is a vertical cross sectional drawing looking along line 6—6 of FIG. 3 showing the shape of the converging internal recess in the IOL double folding member adjacent the opening of the recess;

FIG. 7 is a vertical cross sectional drawing looking along line 7—7 of FIG. 3 showing the shape of the converging internal recess in the IOL double folding member further from the opening of the recess;

FIG. 12 is a plan view of a distal end region of the IOL insertion tube, showing in broken lines the double folded IOL just upstream of an exit end of the tube;

FIG. 13 is a transverse cross sectional drawing looking along line 13—13 of FIG. 12, showing the flattened-oval cross sectional shape of the IOL insertion tube and showing the double folded IOL curled inside the tube;

FIG. 14 is a longitudinal cross sectional drawing looking along line 14—14 of FIG. 12, showing the double folded IOL pushed in the direction of Arrow "A'" by a piston disposed in the tube so that the double folded IOL is axially positioned just upstream of an angled opening at the distal end of the IOL insertion tube;

FIG. 15 is a longitudinal cross sectional drawing similar to FIG. 14, showing the double folded IOL pushed by the piston further in the direction of Arrow "A'" so that the leading haptic and the leading edge of the optic portion of the double folded IOL are pushed axially out of the angled opening at the distal end of the IOL insertion tube;

FIG. 16 is a longitudinal cross sectional drawing similar to FIG. 15, showing the double folded IOL pushed by the piston still further in the direction of Arrow "A'" so that major portions of the IOL are pushed axially out of the angled opening at the distal end of the IOL insertion tube, and showing the double folded starting to unfold back to its original, unfolded state;

FIG. 20 is a plan view, corresponding generally to FIG. 13, of a distal end region of the IOL insertion tube, showing in broken lines the double folded IOL supported by the axially extending rigid finger of the IOL pushing piston just upstream of an exit end of the tube;

FIG. 21 is a transverse cross sectional drawing, corresponding generally to FIG. 13, looking along line 21—21 of FIG. 20, showing the oval cross sectional shape of the IOL insertion tube and showing the double folded IOL supported by the axially extending rigid finger of the IOL pushing piston and curled inside the tube;

FIG. 22 is drawing corresponding generally to FIG. 14 and is a longitudinal cross sectional drawing looking along line 22—22 of FIG. 20, showing the double folded IOL supported by the axially extending rigid finger of the IOL pushing piston with the double folded IOL pushed in the direction of Arrow "A'" by the piston so that the double folded IOL is axially positioned just upstream of an angled opening at the distal end of the IOL insertion tube;

FIG. 23 is a longitudinal cross sectional drawing similar to FIG. 22 and corresponding generally to FIG. 15, showing the double folded IOL still supported by the axially extending rigid finger of the IOL pushing piston, with the double folded IOL pushed by the piston further in the direction of Arrow "A'" so that the leading haptic and the leading edge of the optic portion of the double folded IOL are pushed axially out of the angled opening at the distal end of the IOL insertion tube; and FIG. 24 is a longitudinal cross sectional drawing similar to FIG. 23 and corresponding generally to FIG. 16, showing major portions of the double folded IOL still supported by the axially extending rigid finger of the IOL pushing piston, with the IOL pushed by the piston still further in the direction of Arrow "A'" so that major portions of the IOL are pushed axially out of the angled opening at the distal end of the IOL insertion tube, and showing the double folded starting to unfold back to its original, unfolded state.

In the various FIGS., the same elements and features are given the same reference numbers; elements and features in FIGS. 17–24 corresponding to those shown in FIGS. 1–16 are given the same reference numbers followed by an "a".

DESCRIPTION OF THE PREFERRED EMBODIMENT

Figure 1:
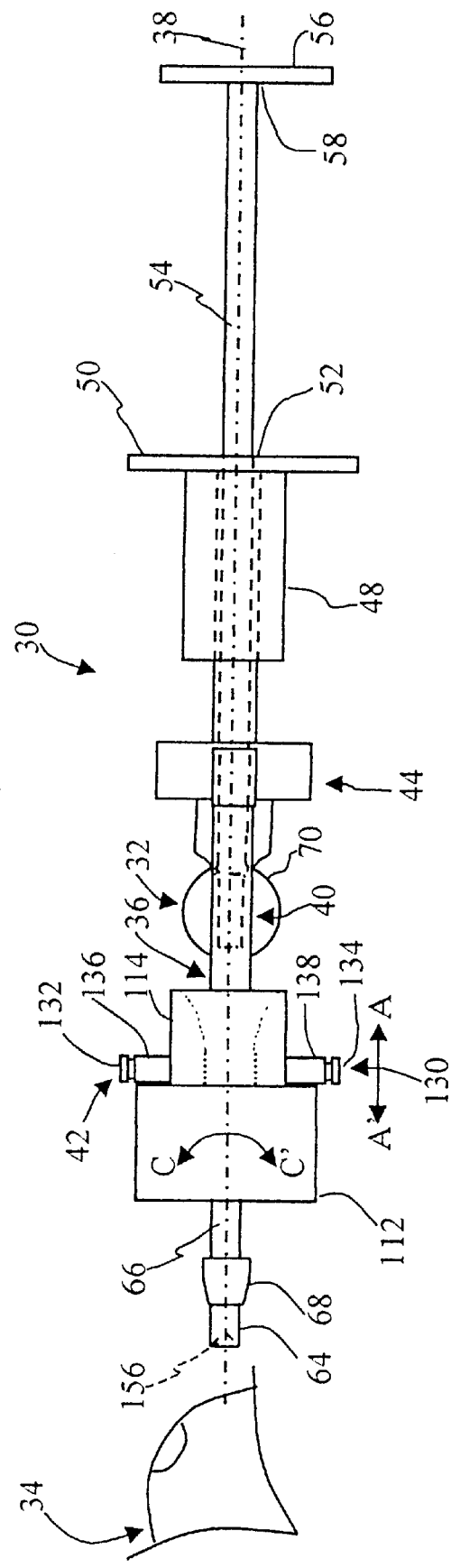
FIG. 1 is a plan view of the anterior chamber intraocular lens (IOL) folding and inserting instrument of the present invention, showing an IOL insertion tube, an IOL receiving and folding station on the insertion tube containing a representative IOL, an axially movable IOL double folding member, a barrel attached to the IOL insertion tube and an IOL insertion piston disposed in the barrel and IOL insertion tube.

An intraocular lens (IOL) folding and inserting or implanting instrument 30, in accordance with the present invention and particularly for implanting an elastically deformable IOL 32 in the anterior chamber of a patient's eye 34, is shown in FIG. 1.

As more particularly described below, instrument 30 comprises an elongate, slender IOL insertion tube 36 having an oval transverse cross section and a longitudinal axis 38. Located within IOL insertion tube 36 is an IOL receiving (holding) and folding station 40 in which is shown representative anterior chamber IOL 32, for example, the type of IOL disclosed in my co-pending application Ser. No. 09/312,566 now U.S. Pat. No. 6,152,959.

Further comprising instrument 30, also as more particularly described below, are IOL double folding means 42 and IOL retaining means 44. IOL double folding means 42 is installed on IOL insertion tube 36 just downstream of IOL receiving and folding station 40 and IOL retaining means 44 is installed on the insertion tube just upstream of the IOL receiving and folding station.

Shown connected to insertion tube 36 at a proximal end region of the tube is a larger diameter barrel 48 having a finger retaining flange 50 at a proximal end 52 of the barrel. As depicted, insertion tube 36 may extend entirely through barrel 48. Axially disposed in barrel 48 and IOL insertion tube 36, and projecting from barrel proximal end 52, is an elongate, slender, rigid IOL pushing piston or plunger 54 formed having a thumb-operating flange 56 at a proximal end 58 of the piston.

As further depicted in FIG. 1, a disposable IOL insertion tube tip 64, preferably constructed of a biocompatible material such as silicone, is detachably attached to a distal end 66 of insertion tube 36, the tube being preferably constructed from stainless steel, so as to be reusable. A connection 68 of tip 64 to tube distal end 66 may, for example, comprise a conventional luer fitting.

Figure 2:
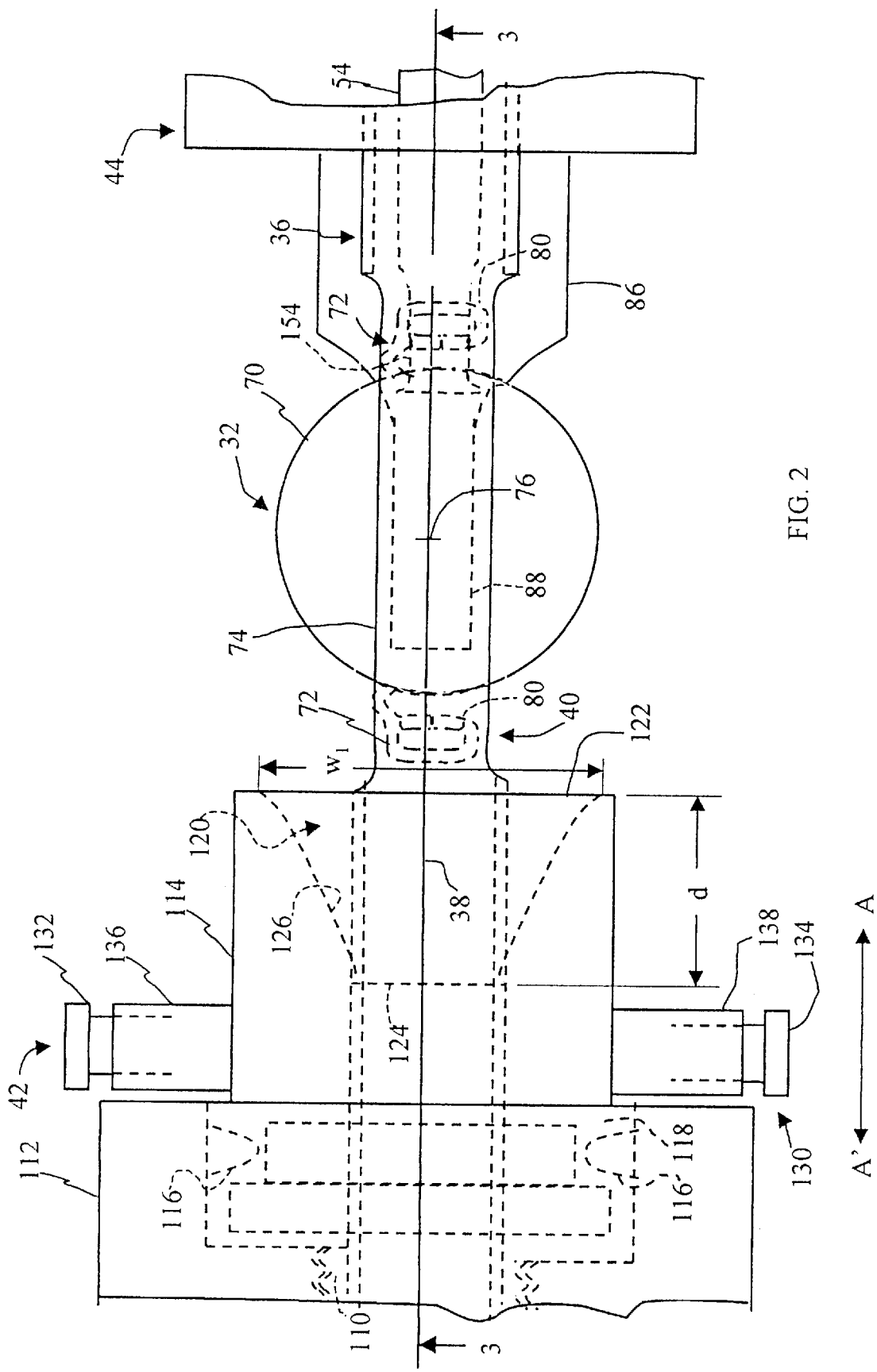
FIG. 2 is a partial, enlarged plan view of the instrument of FIG. 1, showing an IOL received in the IOL receiving and folding region of the IOL insertion tube and showing the axially movable IOL double folding member positioned away from the IOL receiving and folding station.

Representative elastically deformable IOL 32, which forms no part of the present invention, IOL receiving and holding station 40 and parts of IOL double folding means 42, IOL holding means 44 and IOL insertion tube 36 of are shown in more detail in FIG. 2. As shown, IOL 32 comprises a generally circular optic 70 to which is attached an opposing pair of ocular attachment or fixation elements 72, commonly called "haptics." It is to be understood that the double folding of IOL 32 means the double folding of IOL optic 70 that constitutes the major part of the IOL; although, some deformation of haptics 72 may occur as well.

IOL 32 is shown installed in IOL receiving and folding station 40, which comprises a narrow axial upper wall region 74 of IOL insertion tube 36 with adjacent regions of the tube cut away sufficiently to enable installation of the IOL into the station. When (as shown) IOL 32 is correctly installed in station 40, a center 76 of IOL optic 70 and looped ends 80 of haptics 72 are aligned with tube longitudinal axis 38.

As depicted in FIGS. 3 and 4, IOL holding means 44 comprises an IOL holding member 82 that is slidably installed in a guide 84, both of which extend around IOL insertion tube 36 upstream of IOL receiving and holding station 40. IOL Holding member 82 is formed having an elongate central slot 85 that permits the holding member to slide up and down with respect to IOL insertion tube 36.

As seen from FIG. 3, IOL Holding member 82 is constructed having an elongate, upward curving arm 86 that extends axially toward IOL double folding means 42(FIG. 3). Holding member arm 86 terminates in a narrow, slender finger region 88 sized to fit upwardly into IOL insertion tube 36 through a tube opening or cutaway region 90 at IOL receiving and folding station 40.

IOL holding member 82 is vertically slidable in guide 84 (for the instrument orientation shown in FIG. 3) in the direction of Arrows B–B' between a first, retracted position, shown in phantom lines and a second, advanced position, shown in solid lines.

In the first, retracted position of IOL holding member 82, finger region 88 is located below and clear of IOL receiving and holding station 40 a distance sufficient to permit the loading of IOL 32 into the station. In the second, extended position of IOL holding member 82, finger region 88 extends upwardly into tube opening 90 and station 40 until an upper surface 92 of the finger region bears against a lower surface 94 of IOL optic 70 along tube longitudinal axis 38. In this position, finger region 88 presses an upper surface 96 of the optic against an inner surface 98 of tube wall region 74 (see also FIG. 5), thereby holding received IOL 32 securely in place in station 40 during the IOL double folding procedure described below.

As further shown in FIG. 3, IOL double folding means 42 comprises three parts: An externally threaded screw element 110, an internally threaded drive element or nut 112 and an IOL double folding member 114. Externally threaded element 110 is fixed (for example, by brazing or silver soldering processes) to IOL insertion tube 36 in a location downstream of IOL receiving and holding station 40. Internally threaded drive element 112 is threaded onto externally threaded element 110 and is free to rotate thereon in either rotational direction C–C' to cause axial movement in the direction of Arrow A–A'.

IOL double folding member 114 is axially slidably mounted on IOL insertion tube 36, but is constrained against rotation by the cross sectional shape of the tube. Drive element 112 is connected in axially driving relationship to IOL double folding member 114 by a plurality of lugs 116 (two lugs being shown) that are constrained in an annular groove or recess 118 formed around a distal end region of the double folding member. Consequently, rotation of drive element 112 on externally treaded element 110 imparts an axial sliding movement of IOL double folding member 114 along tube 36.

Formed into IOL double folding member 114 is a recess 120 that smoothly converges from a wide opening 122 facing IOL receiving and holding station 40 to the outside size of IOL insertion tube 36 at a recess exit 124. Recess opening 122 has a width, w, of about 8 mm and recess 120 has a depth, d, of about 8 mm.

As shown in the two axially spaced apart vertical cross sections of IOL folding member 114 (FIGS. 6 and 7), recess 120 is defined by a inner surface 126 into a generally key-hole shape having a an upper, generally elliptically-shaped region 128 and a lower opening region 129 sized for sliding over IOL holding member arm 86. Recess 120 is shaped to cause the gradual folding or bending over and under of sides of IOL optic 70 as IOL folding member 114 is axially moved over IOL 32, as described below. To accomplish this, the size of recess 120 diminishes from opening 122 toward recess exit 124 (FIG. 2).

IOL double folding means 42 advantageously includes IOL side squeezing means 130 that comprises first and second, spring-loaded IOL fold squeezing or tightening members 132 and 134 transversely slidably disposed in respective guides 136 and 138 mounted through opposing side regions of IOL double folding member 114 at a distal end region thereof (FIGS. 1, 2, 5 and 8). As described below, IOL fold squeezing members 132 and 134 function to squeeze IOL optic 70, after it has been double folded by member 114, into a tighter double fold, as may be desirable or needed for higher diopter (that is, thicker) IOL optics 70 for fitting the IOL into IOL insertion tube 36.

The IOL double folding procedure using instrument 30 (which may be facilitated by the application to tube 36, IOL 32 and folding member 114 of a viscoelastic solution lubricant suitable for use in human eyes) is depicted in FIGS. 8–11.

Figure 8:
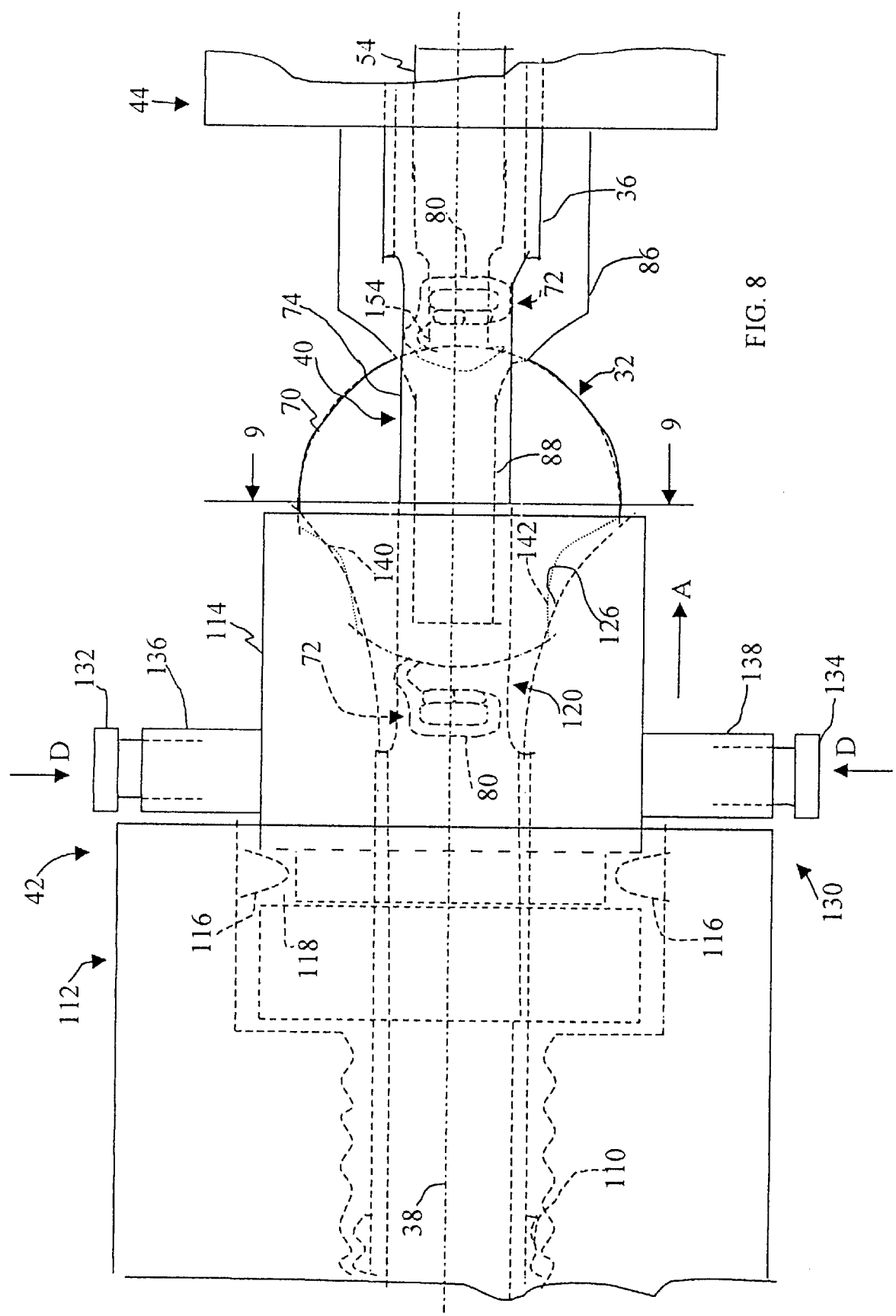
FIG. 8 is a partial, enlarged plan view of the instrument, similar to FIG. 2, showing the IOL double folding member axially moved into initial folding engagement with the IOL received in the IOL receiving and folding station and showing partial folding of the IOL.

As shown in FIG. 8, IOL double folding member 114 is axially moved (in the direction of Arrow "A"), by rotation of drive element 112 on externally threaded element 110, along IOL insertion tube 36 partially onto IOL receiving and holding station 40. In this axial position of IOL double folding member 114, inner surface 126 of double folding member recess 120 engages opposite side edge regions 140 and 142 of IOL optic 70 and starts bending these side edges under (see also FIG. 9).

Note that in the above-described axial position of IOL double folding member 114, finger region 88 of IOL holding member 82 holds longitudinal central regions of IOL optic 70 against inner surface 98 of tube upper wall region 74.

Figure 10:
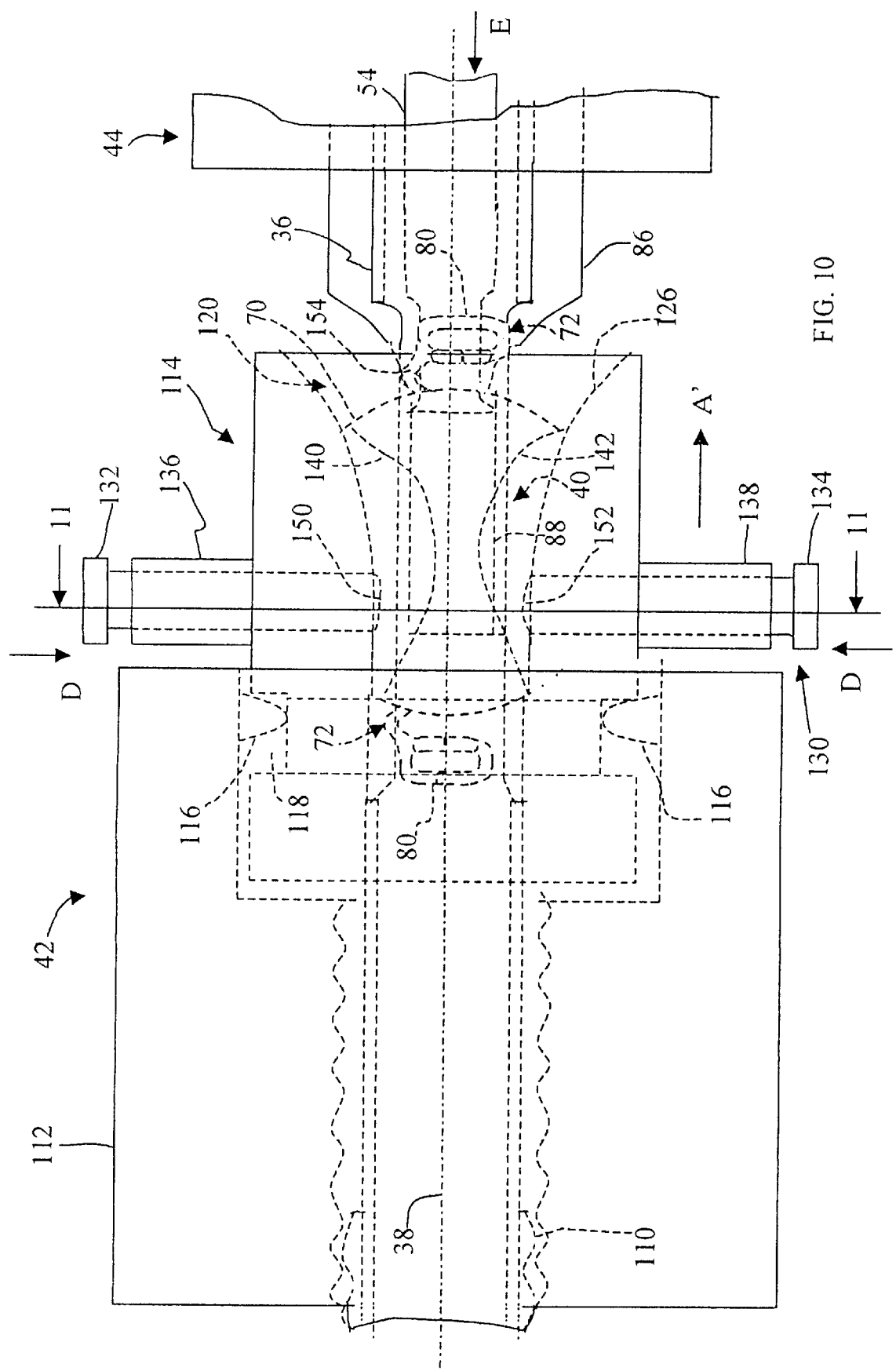
FIG. 10 is a partial, enlarged plan view of the instrument, similar to FIG. 8, showing the IOL double folding member axially moved into substantially complete engagement with the IOL received in the IOL receiving and folding station and showing substantially complete double folding of the IOL.

FIG. 10 shows IOL double folding member 114 moved further axially (direction of Arrow "A") along IOL insertion tube 36 and over IOL receiving and folding station 40 until IOL optic 70 is completely inside IOL double folding member recess 120 and the double folding over of entire optic side edge regions 140 and 142 is nearly completed by engagement with recess surface 126.

Figure 11:
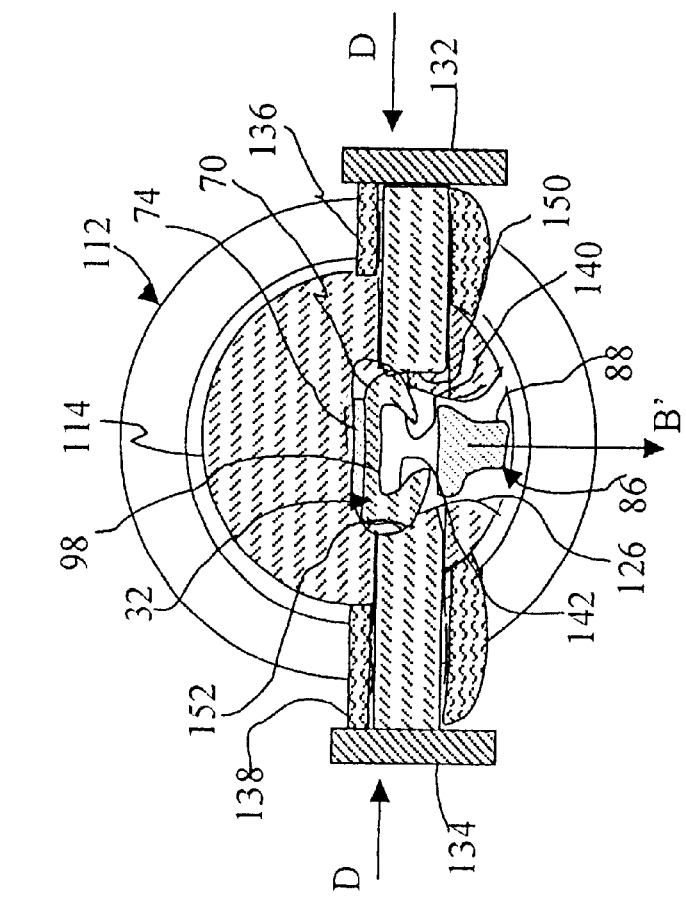
FIG. 11 is a transverse cross sectional drawing, similar to FIGS. 6 and 9, looking along line 11—11 of FIG. 10 showing the double folding of the IOL held in the IOL holding and folding station and showing the transverse IOL compressing member associated with the IOL double folding member actuated to transversely compress the double folded IOL.
Figure 9:
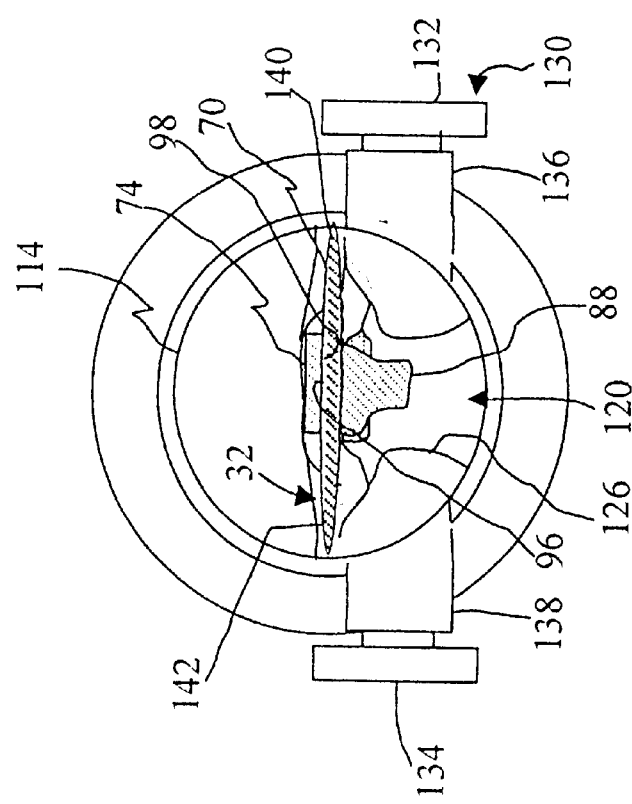
FIG. 9 is a transverse cross sectional drawing, similar to FIG. 6, looking along line 9—9 of FIG. 8 showing the initial folding stage of the IOL held in the IOL holding and folding station.

In this axial position of IOL double folding member 114, pressing members 132 and 134 are pushed sidewardly (inwardly) in the direction of Arrows "D". As shown in e FIG. 11, respective inner ends 150 and 152 of pressing members 132 and 134 are thereby pressed against respective edge regions 140 and 142 of IOL optic 70 to squeeze the optic into a tighter C-shaped double fold. Also as shown in FIG. 11, holding arm 86 has, for this axial position of IOL folding member 114, been lowered (direction of Arrow "B'") so that finger region 88 is out of the way of the double folding operation.

As shown in FIG. 12 (also in FIGS. 2, 8 and 10), a notched distal end 154 of piston 54 is engages a trailing edge of IOL optic 70. When IOL optic 70 is double folded by IOL double folding member 114, piston 54 is axially pushed in the direction of Arrow "A'" to push double folded IOL 32 through IOL insertion tube 36 and into detachable insertion tip 64.

FIG. 13 depicts, in transverse cross section, IOL 32, specifically IOL optic 70, double folded into a tight C-shape inside insertion tip 64 that is oval in shape with substantially flat upper and lower wall regions. Insertion tip 64 that preferably has a wall thickness, t, of about 0.15 mm, also preferably has an outside width, $w_2$, of about 3.2 mm, an outside height, h, of about 1.5 mm, to enable the tip to be inserted through a small ocular incision no greater than about 3.2 mm.

As shown in FIG. 14, the double folded IOL 32 has been axially pushed through insertion tip 64 until a leading one of IOL haptic end loops 80 is at a beveled distal end 156 of insertion tip 64. Distal end 156 is angled at an angle, a, of between about 30 and about 60 degrees, and preferably at about 45 degrees, to permit the relatively gradual and controlled unfolding of double folded IOL 32 in a patient's eye (FIGS. 15 and 16).

FIGS. 14–16 also show that a lower region of piston distal end 154 is cut away to provide clearance for the trailing one of IOL haptics 72.

As described above, relative to FIGS. 1–16, the double folding of IOL 32, that is, of IOL optic 70, is accomplished by axially advancing IOL double folding member 114 over (onto) IOL 32 that is held stationary in IOL receiving and folding station 40 by holding arm finger region 88. Stated otherwise, the IOL double folding is accomplished by the interaction of IOL 32 with IOL double complished by the interaction of IOL 32 with IOL double folding member recess surface 126.

Variation Instrument of FIGS. 17–24

Since the engagement between IOL double folding member recess surface 126 and IOL 32 (optic 70) causes the IOL double folding, it is immaterial to the present invention whether the IOL remains stationary and the IOL double folding member moves over the IOL (as described above) or whether the IOL double folding member remains stationary and the IOL moves into the double folding member (as described below).

Figure 17:
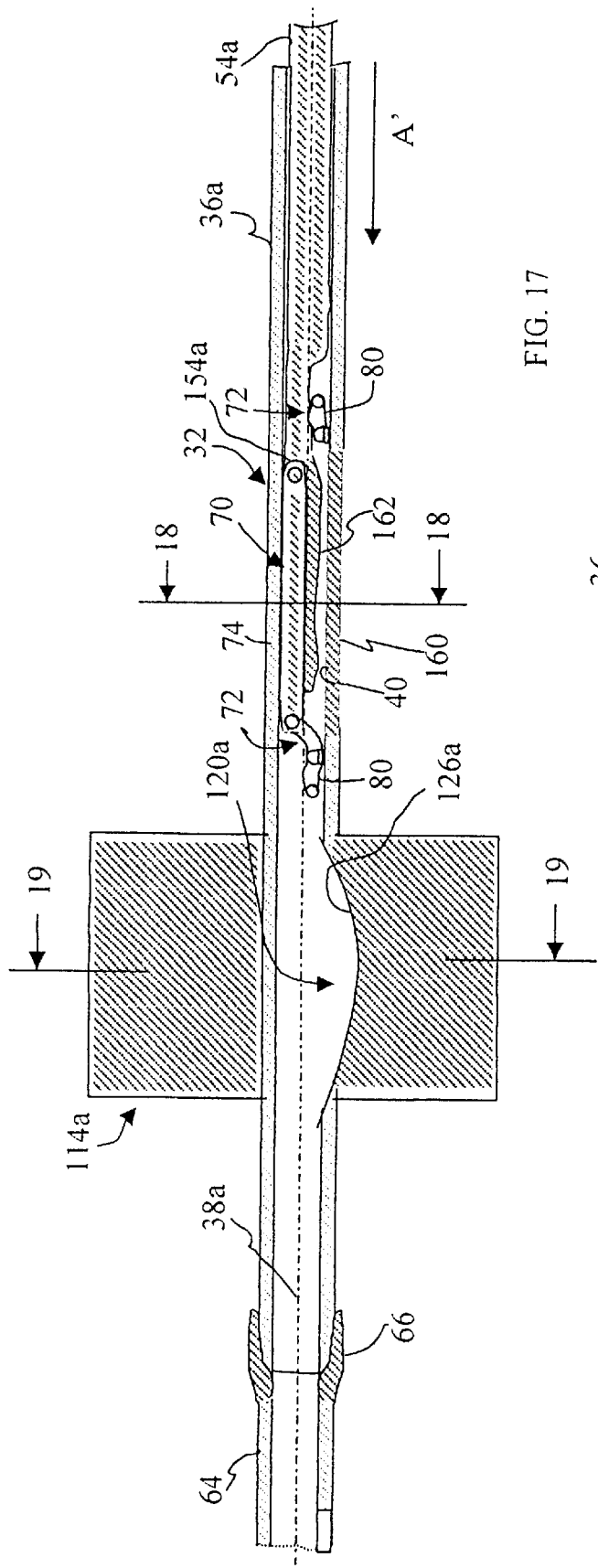
FIG. 17 is a longitudinal cross sectional drawing of a variation IOL double folding instrument, generally corresponding to FIG. 3, showing an unfolded IOL received in an IOL receiving station in an IOL insertion tube, showing a central region of the received IOL held against an inner wall surface of the IOL insertion tube by a slender, axially extending rigid finger at a distal end of an IOL pushing piston disposed in the tube, and further showing an IOL double folding member fixed to the tube downstream of the IOL receiving station.
Figure 18:
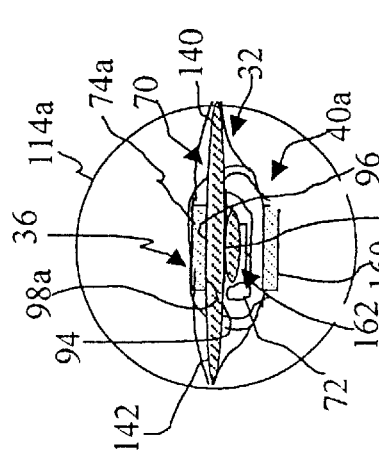
FIG. 18 is a transverse cross sectional drawing, corresponding generally to FIG. 4, looking along line 18—18 of FIG. 17, showing the unfolded IOL held in the IOL holding and folding station by the axially extending rigid finger of the IOL pushing piston.
Figure 19:
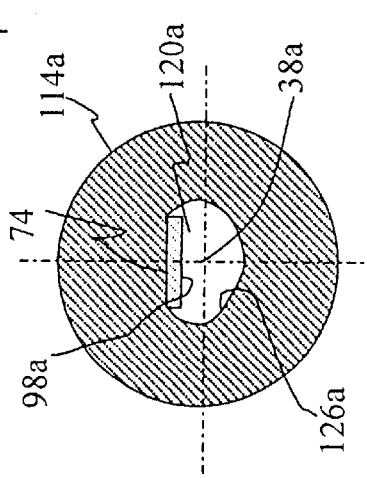
FIG. 19 is a transverse cross sectional drawing looking along line 19—19 of FIG. 17 showing the shape of the converging internal recess in the IOL double folding member.

A variation IOL folding and inserting or implanting instrument 30a, is described below in conjunction with FIGS. 17–24. As shown in FIG. 17, instrument 30a comprises an elongate IOL insertion tube 36a that is the same, except as noted, as above-described tube 32. Formed in tube 36a is an IOL receiving station 40a that corresponds to above-described IOL receiving and folding station 40, and in which IOL 32 is shown. IOL receiving station 40a is formed by cutting away opposite side regions insertion tube 36a leaving an upper wall region 74a (corresponding to above-described tube wall region 74) and a lower wall region 160. As a result, IOL 32 is loaded into station 40a through one of the open sides of tube 36a and, when correctly positioned in the station, opposite side regions 140 and 142 of IOL optic 70 extend through the open sided of the tube (FIG. 18).

IOL pushing piston 54a is formed having an IOL pushing region 154a that corresponds directly to above-described region 154 of piston 54. However, extending axially in a downstream direction from piston region 154a is an elongate, slender IOL support region 162 (FIGS. 17 and 18). An upper surface 164 of IOL support region 162 bears against lower surface 94 of IOL optic 72 and holds a central region of the optic against tube region 74 during the double folding procedure, as described below. In that respect IOL support region 162 serves the same function as above-described IOL holding member finger 88.

Fixed to IOL insertion tube 36a, downstream of IOL receiving station 40a, is a IOL double folding member 114a (FIGS. 17 and 19) that corresponds generally to above-described IOL double folding member 114, except that member 114a is fixed to tube 36a against both axial and rotational movement. Formed in IOL double folding member 114a and defined by an inner surface 126a is an IOL double folding recess 120a (FIG. 19) that corresponds to upper region 128 of recess 120 (FIGS. 6 and 7).

In instrument 30a, the double folding of IOL 32 (that is, of IOL optic 70) is accomplished by axially moving the IOL (in the direction of Arrow A') in IOL insertion tube 36a into IOL double folding member recess 120a (FIGS. 17 and 20). This IOL movement is done by moving by piston 54a in the axial direction of Arrow A', with a notched end of piston distal end region 154a pushing against a trailing edge of IOL optic 70, and with IOL support region 162 holding the optic against tube wall 74a.

FIGS. 20–24, which correspond to above described FIGS. 12–16, depict double folded IOL 32 in the process of being pushed through IOL insertion tip 64 toward and out of insertion tip beveled end 156. It is seen in these FIGS. 20–24 that IOL support region 162 of piston end region 154a continues to support IOL optic 70 even as IOL 32 is discharged from insertion tip 64.

It is thus seen from FIGS. 1–16, and their accompanying description, that IOL 32 (that is, IOL optic 70) is double folded into a tight C-shape by axially moving IOL double folding member 114 axially along IOL insertion tube 36 onto and over the IOL that is kept stationary during the double folding process. Conversely, it is seen from FIGS. 17–24, and their accompanying description, that IOL 32 (that is, IOL optic 70) is double folded into a tight C-shape by axially moving the IOL axially along IOL insertion tube 36a into IOL double folding member 114a that is kept stationary.

Although not shown, IOL double folding member 114a may include above-described IOL side squeezing means 130 that functions as described above to tighten the general C-shaped double fold of IOL 32.

Although there has been described above an IOL insertion instrument, and a variation thereof, especially for the insertion of small incision, elastically deformable anterior chamber IOLs, in accordance with the present invention for purposes of illustrating the manner in which the present invention maybe used to advantage, it is to be understood that the invention is not limited thereto. Consequently, any and all variations and equivalent arrangements that may occur to those skilled in the applicable art are to be considered to be within the scope and spirit of the invention as set forth in the claims, which are appended hereto as part of this application.

What is claimed is:

1. An instrument for double folding an elastically deformable intraocular lens (IOL) and for inserting said double folded IOL into the anterior chamber of a patient's eye for controlled unfolding, said instrument comprising:

a. an elongate, slender IOL insertion tube having a distal end and a longitudinal axis;

b. an IOL receiving station located in said tube adjacent a cutaway opening in the tube;

c. a support element configured for holding a central optic region of an IOL received in said IOL receiving station against an inner surface of said tube during double folding of said IOL;

d. an IOL double folding member installed on said tube, said IOL double folding member having a converging recess facing said IOL receiving station, said recess being along the tube longitudinal axis and having an IOL discharge opening facing the IOL insertion tube distal end; and e. means for causing relative axial movement between an IOL received in said IOL receiving station and said IOL double folding member to cause the double folding of said IOL into a general C-shape.

2. The instrument as claimed in claim 1, including a disposal IOL insertion tip detachably attached to the distal end of the IOL insertion tube.

3. The instrument as claimed in claim 2, wherein said IOL insertion tip is flexible and is constructed of a silicone or an acrylic material.

4. The instrument as claimed in claim 2, wherein at the IOL insertion tip has an oval cross section having an external width between about two times and three times greater than an external height of the insertion tip.

5. The instrument as claimed in claim 4, wherein the IOL insertion tip is sized for insertion through an ocular incision no greater than about 3.2 mm.

6. The instrument as claimed in claim 2, wherein the distal end of said IOL insertion tip is beveled at an angle between about 30 degrees and about 45 degrees.

7. The instrument as claimed in claim 1, including a piston axially slidably disposed in said tube for axially pushing said double folded IOL through the distal end of said tube.

8. The instrument as claimed in claim 1, wherein said IOL folding member is axially movable on said tube.

9. The instrument as claimed in claim 8, wherein said means for causing relative axial movement between said IOL and said IOL folding member is connected for causing said IOL folding member to move axially along said IOL insertion tube so that said converging recess moves onto the IOL received in said IOL receiving station member for thereby causing the double folding of the IOL received in said IOL receiving station.

10. The instrument as claimed in claim 9, wherein said means for causing relative movement includes a drive member threadably connected to said tube and in driving engagement with said IOL folding member for causing axial movement of the IOL double folding member.

11. The instrument as claimed in claim 8, wherein said support element includes an IOL support member movable between a first position in which said support element permits the insertion of an IOL into said IOL receiving station through said tube cutaway opening and a second position in which said support element holds a central optic region of said IOL against said tube inner surface parallel to said tube longitudinal axis.

12. The instrument as claimed in claim 8, including means cooperating with said IOL folding member for exerting a side pressure on said IOL after being double folded in a general C-shape to thereby compress said double folded IOL into a tighter C-shape.

13. The instrument as claimed in claim 1, wherein said IOL double folding member is fixed to said IOL insertion tube and wherein said means for causing relative axial movement between an IOL received in said IOL receiving station and said double folding member causes the IOL received in the IOL receiving station to be moved axially through said IOL insertion tube into the converging recess of said IOL double folding member.

14. The instrument as claimed in claim 13, wherein said means for causing relative axial movement comprises a piston axially slidably disposed in said tube, a distal end of said piston being configured for engaging an edge of an optic portion of an IOL received in said receiving station.

15. The instrument as claimed in claim 14, wherein said support element comprises a slender, axial projection at said piston distal end.

16. An instrument for double folding an elastically deformable intraocular lens (IOL) and for inserting said double folded IOL into the anterior chamber of a patient's eye for controlled unfolding, said instrument comprising:
   a. an elongate, slender IOL insertion tube having a distal end and a longitudinal axis;
   b. an IOL receiving and folding station located inside said tube adjacent a side opening in the tube, said IOL receiving and folding station being configured for receiving an IOL, having an optic and haptics attached to opposing edges of said optic, with said haptics generally aligned with said IOL insertion tube longitudinal axis;
   c. an IOL double folding member axially movably mounted on said IOL insertion tube, said IOL double folding member having a converging recess facing said IOL receiving and folding station and an IOL discharge opening facing the distal end of said tube, said recess being along the longitudinal axis of the tube;
   d. a driver coupled between said IOL insertion tube and said IOL double folding member for causing movement of said IOL double folding member axially along said IOL insertion tube between a first axial position in which said member is out of engagement with an IOL received in said IOL receiving and folding station and a second axial position in which said member causes the double folding of an IOL received in said station into a general C-shape; and
   e. means for axially pushing a double folded IOL positioned in said IOL receiving and folding station through the IOL double folding member discharge opening and the distal end of said tube.

17. The instrument as claimed in claim 16, including an IOL support member having an IOL support element, said support member being movable between a first position in which said support element permits the insertion of an IOL into said IOL receiving and folding station through said tube cutaway opening and a second position in which said support element holds a central optic region of said IOL against an inner surface of said tube parallel to said tube longitudinal axis as the IOL is double folded.

18. The instrument as claimed in claim 16, including means cooperating with said IOL folding member for exerting a side pressure on said IOL after being double folded into a general C-shape to thereby compress said double folded IOL into a tighter C-shape.

19. The instrument as claimed in claim 16, including a disposable IOL insertion tip and means for detachably attaching said insertion tip to the IOL insertion tube distal end, said insertion tip having an oval transverse cross sectional shape with an external width that is about 2 to about 3 times greater than an external height, a wide region of said insertion tip being thereby formed; the insertion tip being sized for insertion through an ocular incision no greater than about 3.2 mm.

20. The instrument as claimed in claim 19, wherein the wide region of said IOL insertion tube distal end is beveled at an angle between about 30 and about 45 degrees.

21. The instrument as claimed in claim 16, wherein said means for axially moving said IOL folding member between said folding member first and second positions includes an externally threaded member fixed to said IOL insertion tube, said driver being threadably installed on said externally threaded element.

22. An instrument for double folding an elastically deformable intraocular lens (IOL) and for inserting said double folded IOL into the anterior chamber of a patient's eye for controlled unfolding, said instrument comprising:
   a. an elongate, slender IOL insertion tube having a distal end and a longitudinal axis;
   b. an IOL receiving station located inside said tube adjacent a side opening in the tube, said IOL receiving station being configured for receiving an IOL, having an optic and haptics attached to opposing edges of said optic, with said haptics generally aligned with said IOL insertion tube longitudinal axis;
   c. an IOL double folding member fixed on said IOL insertion tube, said IOL double folding member having a converging IOL engaging recess with a wide opening facing said IOL receiving station and a discharge opening facing the distal end of the IOL insertion tube, said recess being along said tube longitudinal axis;
   d. a support member configured for holding a central optic region of an IOL received in said IOL receiving station against an inner surface of said IOL insertion tube along a line parallel to said insertion tube longitudinal axis; and
   e. a piston installed in said IOL insertion tube for axially pushing the IOL received in said IOL receiving station along said tube and into said folding member converging recess for causing the double folding of the IOL into a general C-shape, and for thereafter pushing the double folded IOL through the distal end of said tube.

23. The instrument as claimed in claim 22, wherein said support member is formed as an axial projection at the distal end of said piston.

24. The instrument as claimed in claim 22, including a disposable IOL insertion tip and means for detachably attaching said insertion tip to the IOL insertion tube distal, said insertion tip having an oval transverse cross sectional shape with an external width that is about 2 to about 3 times greater than an external height, a wide region of said insertion tip being thereby formed, and being sized for insertion through an ocular incision no greater than about 3.2 mm.

25. The instrument as claimed in claim 24, wherein the wide region of said IOL insertion tube distal end is beveled at an angle between about 30 and about 45 degrees.

* * * * *